United States Patent [19]

Rinard et al.

[11] 4,145,122

[45] Mar. 20, 1979

[54] METHOD AND APPARATUS FOR MONITORING THE POSITION OF THE EYE

[75] Inventors: George A. Rinard; Donald E. Rugg, both of Denver; Dale A. Steffen, Aurora, all of Colo.

[73] Assignee: Colorado Seminary, Denver, Colo.

[21] Appl. No.: 801,459

[22] Filed: May 31, 1977

[51] Int. Cl.² .............................................. A61B 3/10
[52] U.S. Cl. .......................................... 351/7; 351/9; 351/39; 351/158
[58] Field of Search ....................... 351/6, 7, 9, 13, 39, 351/158

[56] References Cited

U.S. PATENT DOCUMENTS

| | | | |
|---|---|---|---|
| 3,379,885 | 4/1968 | Nork ...................................... | 351/6 X |
| 3,689,135 | 9/1972 | Young et al. ........................... | 351/39 |
| 3,724,932 | 4/1973 | Cornsweet et al. .................... | 351/6 X |
| 3,986,030 | 10/1976 | Teltscher .......................... | 250/215 X |
| 4,034,401 | 7/1977 | Mann .................................... | 351/7 X |

Primary Examiner—Paul A. Sacher
Attorney, Agent, or Firm—Edwin L. Spangler, Jr.

[57] ABSTRACT

This invention relates to an apparatus for monitoring the position of the eye and generating an electrical signal based upon its displacement from a neutral position, such apparatus being characterized by a pair of eyeglasses modified to provide an infrared mirror on the inside surface of one lens, an infrared light emitting diode located on the nosepiece in position to produce a virtual image thereof within the wearer's eye as reflected from the infrared mirror, and an image detector mounted on the bow of the eyeglasses adjacent the mirror filtered to respond only to infrared light and effective to locate the position within the eye of the reflected LED image. The invention also encompasses a novel detector which, not only monitors the position of the eye but, in addition, through the use of a photosensor array, provides the means for generating a signal whose magnitude is proportional to the displacement of the eye from its centered or reference position. The invention also encompasses the novel method for tracking eye movements in relation to head position which includes the steps of shining an infrared beam from a position alongside the eye onto an infrared reflective mirror placed in front thereof positioned to reflect said beam onto the cornea and reproduce a virtual image thereof, and tracking said image with a photosensor array filtered to exclude visible light from a position alongside said mirror as said image appears reflected therein.

15 Claims, 2 Drawing Figures

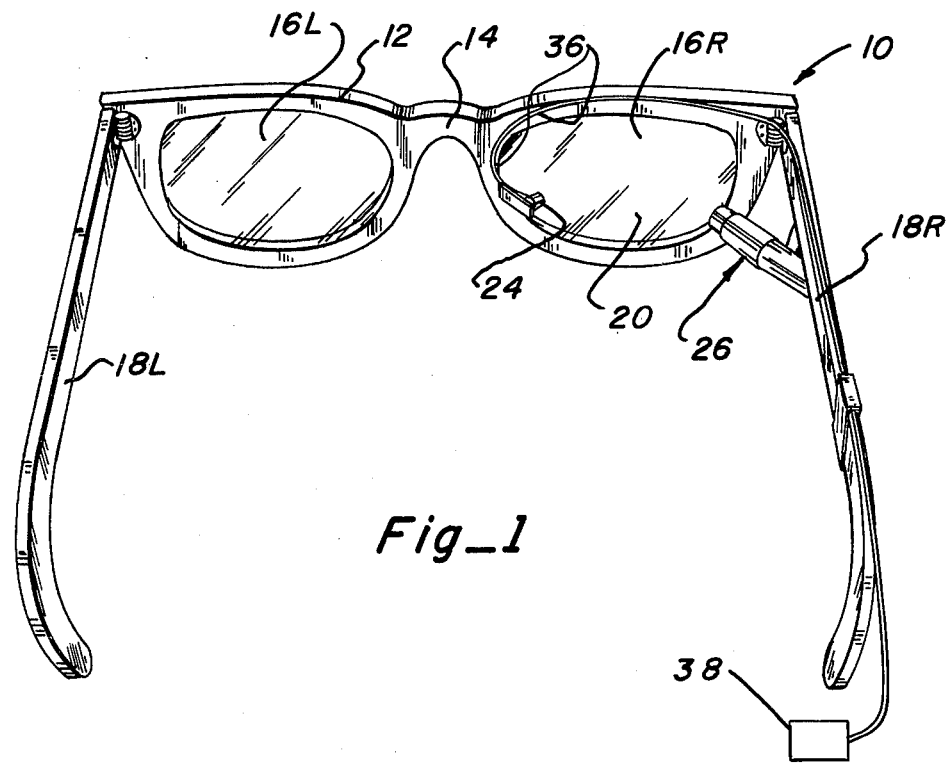
Fig_1
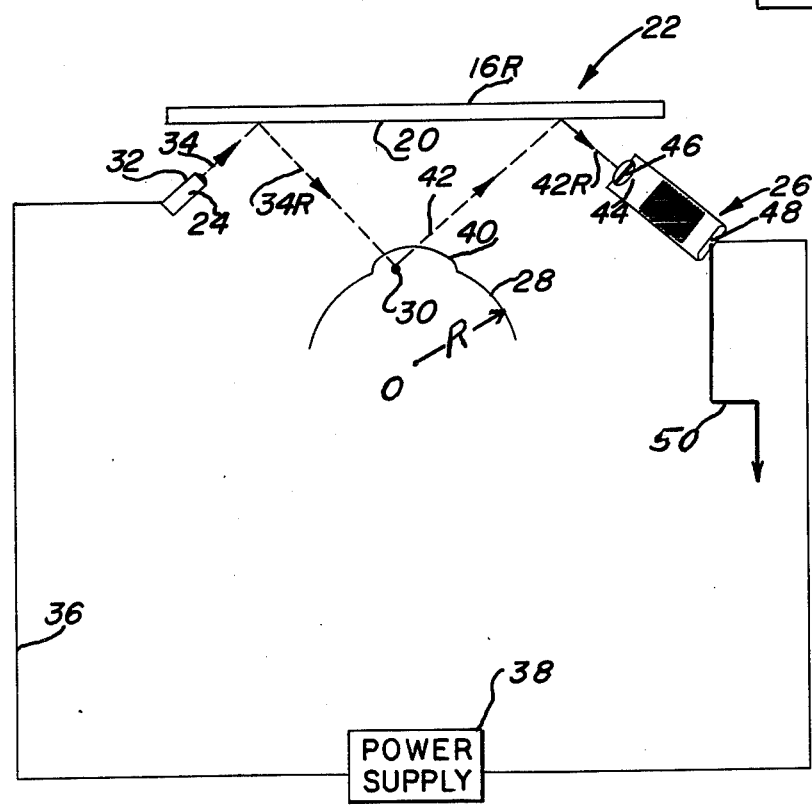
Fig.-2

METHOD AND APPARATUS FOR MONITORING THE POSITION OF THE EYE

The invention described herein was made in the course of work under a grant or award from the Department of Health, Education, and Welfare.

The study of eye motions is an old and well developed art among researchers in the fields of physiology, medicine and other branches of science. For the most part, however, these studies have had as their objective the recordation of eye movements rather than the use thereof in any functional sense. This is not to say that the latter is unknown because this is not the case.

Of the many techniques presently used to measure eye movements, the following is a fairly complete list:
(1) Electro-Oculography
(2) Corneal Reflection
(3) Limbus, Pupil and Eyelid Tracking
(4) Contact Lens Methods
(5) Point of Regard Measurements: Tracking of Corneal Reflection Center with Respect to Pupil Center
(6) Measurement of Eye Rotation by the Double Purkinje Image Method These various techniques are discussed and explained in detail by Young and Sheena in "Survey of Eye Movement Recording Methods" prepared for National Institute of Education, April 1975.

In the above list, probably the most pertinent to that of the instant invention are the so-called "corneal reflex cameras" which, as one might suspect, are based upon the eye movement measurement technique (2). Mackworth and Mackworth in their 1958 article entitled "Eye Fixations Recorded on Changing Visual Scenes by the Television Eye-marker" reported in the Journal of the Optical Society of America extended the basic corneal reflection technique by, so far as applicants known for the first time, mounting an eye movement monitoring camera on the head of the subject. Cameras of this type and for this purpose are commercially available and have been for some time.

The problem with such cameras is two-fold, namely, the weight and complexity of the head mounted apparatus and, secondly, the way in which such equipment interferes with the wearer's normal field of vision. About the only thing that has been done to far to alleviate these problems is to remove the camera itself from the head of the wearer and transfer the visual information thereto by means of a head mounted fiber optic conductor of some sort. While the weight of such apparatus is such less than that of the camera, it remains significant, so significant in fact that it cannot be worn for long periods of time without considerable discomfort. Moreover, the obstruction such equipment places within the field of view of the wearer is still so substantial as to be nearly intolerable.

It has now been found in accordance with the teaching of the instant invention that these and other shortcomings of the prior art structures for monitoring eye movements can be virtually eliminated by the simple, but unobvious, expedient of providing an ordinary pair of eyeglasses with an infrared reflective surface, placing a miniaturized light source to one side thereof out of the normal line of vision but still in a position to introduce an image thereof into the wearer's eye reflected off of the infrared mirror, and detecting the position of the eye by monitoring the position of the light source as it appears in said mirror through a detector mounted alongside thereof that is also outside the range of normal vision. While still head mounted, these components are so small and light that they present no more of a problem for the wearer than the eyeglasses alone. Also, even the mirrored lens remains transparent and, therefore, subject to normal use. In fact, it can even be a prescription lens if the wearer's vision is such as to require correction. An extremely important feature of the instant eye position monitor is the provision of a unique detector which makes it possible to not only locate the position of the eye relative to the head but, in addition, generate electrical signals whose strength bears a predetermined and known relationship to the position of the wearer's eye relative to a reference location. With such a capability, the increase in the number and complexity of the operations the wearer can perform through eye movements alone is greatly extended.

Accordingly, it is, therefore, the principal object of the present invention to provide a novel and improved method and apparatus for monitoring eye movements.

A second object is the provision of a device of the class described in which means are provided for not only locating the position of the eye relative to the head but, in addition, generating an output signal whose magnitude bears a known predetermined relationship to a reference position.

Another object of the within described invention is to provide a head-borne eye position monitor which does not obstruct or otherwise interfere with normal vision.

Still another object is to provide a device of the type aforementioned which, while carried on the patient's head, is virtually no more troublesome or inconvenient than the eyeglasses that define the supporting structure therefor.

An additional object is to provide a mechanism for following the movements of one of the wearer's eyes and outputting an electrical signal predicated upon its movements which can, in turn, be used as a control signal for controlling the function and operation of various types and styles of auxiliary equipment, especially those which the wearer is incapable of operating by any other means.

Further object are to provide an apparatus for monitoring eye movements and generating a signal based upon their position which is simple, lightweight, reliable, easy to master, safe, proven, efficient and even decorative in appearance.

Other objects will be in part apparent and in part pointed out specifically hereinafter in connection with the description of the drawings that follows, and in which:

FIG. 1 is a perspective view showing an ordinary pair of eyeglasses fitted with the eye position monitor of the instant invention; and, FIG. 2 is a diagram showing the eye position monitor in relation to the eye of the wearer.

Referring next to the drawings for a detailed description of the present invention and, initially, to FIG. 1 for this purpose, reference numeral 10 has been chosen to designate broadly a pair of ordinary eyeglasses of the type having a frame 12 including a nosepiece 14, right and left lenses 16R and 16L, respectively, and right and left bows 18R and 18L. One of the lenses, in this case left lens 16L, is conventional while the right lens 16R is modified to include coating 20 on the rear or inside face thereof effective to produce an infrared reflective surface or mirror thereon. Either lens or both may be ground to the wearer's prescription or, alternatively, include no correction. The infrared mirror 20 is essentially transparent to all light within the spectral range of the human eye and, therefore, there is essentially no impairment of the wearer's normal vision. Obviously, infrared mirror 20 will have the same curvature as the inside surface of the lens 16R upon which it is coated; however, as will appear presently, this causes no problem because the eye movement monitoring apparatus of the present invention is readily adjusted to accommodate any such curvature.

The foregoing eye position monitoring aparatus which forms the subject matter of the instant invention has been broadly designated by reference numeral 22 and it will be described in detail in connection with both FIGS. 1 and 2 to which detailed reference will next be made. As indicated in FIG. 2, infrared mirror 20 forms an integral part of the eye movement monitoring device as does the source of infrared light 24 and what has been broadly designated by numeral 26 as a "detector" that locates the position of the wearer's right eye 28 based upon the position of the reflected image 30 of the source 24 it sees in mirror 20.

Infrared light source 24 comprises an infrared light emitting diode (LED) of conventional design, the particular one shown being a GaAs type having an illumination angle between half power points of 35 degrees or less. This light source (LED) is housed in a small case 32 (FIG. 2) fastened alongside mirror 20 tilted so as to direct an infrared beam 34 thereagainst. In the particular form shown in FIG. 1, the LED is fastened to the nosepiece 14 of the eyeglass frame 12 while the detector 26 is mounted on the opposite side of mirror 20 on right bow 18R. Power to operate the LED is supplied by conductor 36 strung along the top of lens 16R out of the line of the wearer's vision and back along bow 18R to portable power supply 38 which, among other things, includes a photosensor array driver.

It should, perhaps, be noted that the eye position monitor of the instant invention is, by no means, restricted to use by wheelchair patients. Instead, it is equally adaptable for use by bed ridden ones and could, for instance, provide them with the means for attending to some of their own personal needs such as, for example, raising and lowering their beds; turning various electrical items on and off like, for instance, room lights, radios, TV sets; closing blinds and draperies; and, even signalling for assistance.

Next, with specific reference to the diagram of FIG. 2, it can be seen that the eye is illuminated by the infrared source 24 as reflected off the infrared mirror 20. More specifically, the reflection of beam 34 (34R) is reflected by the surface of the cornea 40 of the eye 28 and a virtual image 30 thereof is formed about 4mm behind the curved corneal surface. The cornea has a spherical surface covering about 45° of the eye and its radius of curvature is approximately 8mm.

Returning again to FIGS. 1 and 2, it will be seen that detector 26 is carried by the right-hand bow 18R of the spectacle frame 12 on the opposite side of mirror 20 from the infrared light source 24. It also lies outside the field of view of the wearer and is tilted to intercept the beam 42R reflected off the surface of mirror 20 from the eye. The locations of the LED and detector can, of course, be reversed; however, since the LED is much the smaller of the two it is preferably mounted on the nosepiece where there is less room available than on the bow. More will be said presently concerning the orientation of detector 26 relative to this reflected beam as it is the key to initiation of a response keyed in some fashion to the displacement of this image within the eye from a preselected reference or neutral position.

Detector 26 consists of a suitable housing 44 in the forward end of which is mounted a lens 46 or group thereof capable of producing an image of the LED as "seen" by the detector on the surface of mirror 20 at the place within the housing where infrared-responsive sensor 48 is located. Additionally, some means is required to block, or at least limit, the ambient light that reaches the infrared-responsive sensor within the detector, yet, permits the latter to receive the infrared image from within the cornea. Such a means can take either one of two different forms, namely, a visible light absorbing filter or an infrared bandpass filter, both of which accomplish the desired objective.

Sensor 48, in the particular form shown, comprises a photosensor array responsive not only to the presence of the infrared signal but its location as well. While such an array represents a high degree of sophistication in the art of monitoring eye movements, it is by no means essential. As a matter of fact, the selfsame reflectance system can be used to advantage with a single simple photocell where responses are initiated, continued or discontinued solely on the basis of the presence of the reflected image without regard to its location. Timed periods when the eye is closed, sequences of eye closings and openings, or both, add a further dimension to even the single photocell.

The photosensor array that constitutes sensor 48 has, in practice, been made up of some 1024 elements arranged in a square pattern 32 on a side. The eye 28 actually moves about an axis passing through point O in the diagram of FIG. 2. The eye radius R is about twice the radius of the spherical surface of the cornea 40. For this reason, the reflection of the LED which is "seen" by the photosensor array 48 on the surface of mirror 20 moves roughly half the distance that the pupil of the eye moves. It follows, therefore, that the position of the LED image on the surface of the array provides a reasonably accurate picture of the position of the eye relative to the head. It becomes a simple matter then to generate an output signal available at 50 for control purposes whose magnitude is proportional to the displacement of the eye either horizontally (x-axis) or vertically (y-axis) or a combination of the two from a known null or reference position, the latter usually being that in which the patient is looking straight ahead, i.e. the so-called "central gaze position". Other reference positions can, of course, be chosen; but, they have the disadvantage of limiting the excursion of the eye in certain directions along with the magnitude of the signal associated with such movement.

One other important, though non-essential, feature remains and that is to orient the detector relative to the mirror such that the reflected image is centered within the array when the eye is looking straight ahead assuming the latter has been chosen as the reference position. This alignment procedure obviously results in the maximum utilization of the array since the reflected image can move the greatest distance in any direction as can the eye in actuating same.

In actual practice, the eye position monitor described above is adjusted to the individual by displaying the output signal of the photosensor array on an oscilloscope and adjusting the position of the image sensor unit. The sensor unit is adjusted so that the bright spot, which is the corneal reflection is near the center of the array when the eyes are in the central gaze or preselected reference position. The user should be able to move the bright spot from side to side and top to bottom of the array when adjustment is completed.

The eye position monitor of the present invention has been successfully used for the proportional control of an electric wheelchair and the operation of a wheelchair recliner. Each element of the 32 × 32 photosensor array was sequentially addressed by image sensor scanning circuitry to determine if its video signal was in a low or a high state. The array was scanned in about 2 ms and the scan was repeated every 32 ms. The video signals and corresponding addresses were processed by corneal reflection signal detector circuitry which forms no part of the present invention. The corneal reflection was assumed to be detected if two adjacent elements were illuminated if the total number of illuminated elements were sixteen or less and if an arbitrarily selected number of elements produced a signal level above an arbitrary threshold. If these conditions were met, the x and y position coordinates of the corneal reflection were stored in address latch registers. The x and y digital addresses were then converted to proportional control signals which were used to steer an electric wheelchair. The y digital address was also converted to a control signal which was used to operate the wheelchair recliner.

If the corneal reflection is not detected, the eye tracking signal is lost and after 0.25 seconds, the device being controlled was momentarily turned off and if the loss of signal continued for 2.5 seconds, it was latched off. Since closing the eye results in loss of signal, the user can, therefore, stop any operation in 0.25 seconds by merely closing his or her eye. A coded sequence of eye blinks of 1.0 seconds duration or longer was selected as the means of activating the desired mode of operation. A low level audio tone was chosen to inform the user of the mode of operation and to assist in activating the desired mode. Although only two modes of operation, wheelchair control and recliner control were tried, additional modes to operate other equipment could have been added.

In operation, the eyeglasses are placed on the patient and the wheelchair is readied for operation. At the start of the procedure, the control circuitry is always in the null mode. A low amplitude audio beep occurs at a 1 Hz rate to indicate the null mode and to indicate that the eyes are in the preselected central gaze position. To activate the recliner mode, the patient must perform a particular sequence of eye blinks in synchronism with the audio beep. When the recliner mode is activated, a 2 second staccato tone is heard, followed by silence. At this time, no motion occurs because the eyes must be in the central gaze position during the selection of any mode. Looking above the central gaze position causes the wheelchair to recline and looking below central gaze position causes the chair to return to the upright position. The recliner can be stopped in any position by returning the eyes to central gaze or by creating a loss of signal by closing the eye. The recliner mode can be turned off at any degree of reclination by closing the eye for longer than 2.5 seconds. The blink sequence can then be used, when desired, to reactivate the mode. Limit switches stop the motion when the wheelchair is fully reclined or upright.

The recliner had to be in the upright position before the wheelchair drive mode could be activated. Turning on the drive mode was achieved by a different sequence of blinks performed in synchronism with the audio beep. When the drive mode was selected, a 2 second tone was sounded followed by silence. If the eyes remained in the central gaze position, the wheelchair did not move. The velocity of the wheelchair was controlled by the direction and distance that the eyes moved from the central gaze position.

The ocular control is equivalent to a proportional joystick control where looking above and below central gaze corresponds to forward and back movements of the stick, respectively. The wheelchair can be stopped by returning the eyes to central gaze or by closing the eye. The drive mode is turned off, just as the recliner mode, by closing the eye for 2.5 seconds or longer.

Finally, the instant invention encompasses the unique method for monitoring eye movements in relation to head position which consists of the steps of shining an infrared beam from a position alongside the eye onto the surface of an infrared mirror positioned infront thereof so as to reflect the beam onto the cornea and reproduce a virtual image of the beam inside the eye, and then tracking the image thus produced by tracing the movements of the reflection thereof as it appears in the mirror from a position outside the range of normal vision. The visible light should be selectively filtered while allowing light in the infrared range of the spectrum to pass into the detector used to trace the movements of the reflected image.

What is claimed is:

1. For use in combination with a pair of eyeglasses of the type having lenses mounted within a frame that includes a centrally-located nosepiece and bows extending rearwardly from the opposite side margins thereof, the eye position monitor which comprises: infrared reflective means coated upon a surface of one lens so as to cooperate therewith in defining a mirror; a source of infrared light mountable upon said eyeglass frame to one side of said one lens, said source being effective when properly positioned to direct a beam of infrared light against the surface of said mirror and reflect same onto the cornea of the eye of a person wearing said eyeglasses so as to reproduce a virtual image therein that changes position upon movement of the eye relative to the head; and, means comprising an infrared sensitive detector mountable upon said frame on the opposite side of said one lens from the side occupied by the source of infrared light, said detector being positionable to receive the reflection off the surface of the mirror of said virtual image within the eye, and said detector including a sensor responsive to infrared light operative in the presence of said reflected image to generate an output signal.

2. The eye position monitor as set forth in claim 1 wherein the source of infrared light comprises a light emitting diode.

3. The eye position monitor as set forth in claim 1 wherein the sensor comprises an essentially planar array made up of a plurality of photosensors capable of tracking the movement of the reflected image over the surface thereof.

4. The eye position monitor as set forth in claim 1 wherein the infrared reflective coating is essentially transparent to light in the visible spectrum of the human eye.

5. The eye position monitor as set forth in claim 1 wherein the detector includes means interposed between the mirror and sensor effective to pass light within the infrared end of the spectrum while blocking the ambient light outside the latter.

6. The eye position monitor as set forth in claim 1 wherein the source of infrared light is mounted upon the nosepiece of the eyeglass frame and the detector is mounted upon the bow thereof adjacent the coated lens.

7. The eye position monitor as set forth in claim 3 wherein said array of photosensors is operative to output electrical signals whose magnitude bears a known relationship to the degree in which the eye is shifted away from a preselected reference position.

8. The eye position monitor as set forth in claim 3 wherein the area encompassed by said array is sufficient to encompass the shift in the reflected image over essentially the full range of eye movements.

9. The eye position monitor as set forth in claim 3 wherein the detector includes lens means interposed between the mirror and sensor, said lens means being effective to reproduce a focused image of said reflected image in essentially coplanar relation to said photosensor array.

10. The eye position monitor as set forth in claim 7 wherein the magnitude of the electrical signal is proportional to the displacement of the reflected image on the photosensor array from the position said image occupies thereon when the eye lies in its preselected reference position.

11. The improved method for tracking eye movements relative to the head which comprises: positioning an infrared reflective mirror in front of one eye; shining a beam of infrared light into said mirror from a position alongside the eye so as to reproduce a virtual image of said beam upon the latter that shifts position upon movement thereof relative to the head, tracing the shift of said image within the eye by noting the movement of the reflected image thereof appearing in the mirror from a second position alongside the eye, and initiating a response predicated upon the shift in said reflected image from the position said image occupies when the eye is in a predetermined reference position relative to the head.

12. The improved method as set forth in claim 11 wherein the initiated response comprises generating an electrical signal whose magnitude is proportional to the distance said reflected image is displaced from said position it occupies with the eye in its predetermined reference position.

13. The method as set forth in claim 11 which includes the step of admitting light within the spectrum visible to the human eye to said eye covered by the infrared reflective mirror.

14. The method as set forth in claim 11 which includes the step of filtering out the ambient light outside the infrared spectrum preparatory to tracing the shift in the reflected image.

15. The method as set forth in claim 11 which includes the step of focusing said reflected image preparatory to tracing the movement thereof.

* * * * *